United States Patent [19]
Lentell

[11] Patent Number: 5,628,792
[45] Date of Patent: May 13, 1997

[54] CARDIAC VALVE WITH RECESSED VALVE FLAP HINGES

[75] Inventor: Jan Lentell, Stockholm, Sweden

[73] Assignee: JCL Technic AB, Stockholm, Sweden

[21] Appl. No.: 660,726

[22] Filed: Jun. 7, 1996

Related U.S. Application Data

[63] Continuation of Ser. No. 302,697, filed as PCT/SE93/00219, Mar. 11, 1993 published as WO93/17637, Sep. 16, 1993, abandoned.

[30] Foreign Application Priority Data

Mar. 13, 1992 [SE] Sweden ................. 9200779

[51] Int. Cl.⁶ ..................................................... A61F 2/06
[52] U.S. Cl. ........................................................ 623/2
[58] Field of Search ................................ 623/2, 900

[56] References Cited

U.S. PATENT DOCUMENTS

| | | | |
|---|---|---|---|
| 3,938,197 | 2/1976 | Milo . | |
| 4,328,592 | 5/1982 | Klawitter | 623/2 |
| 4,406,022 | 9/1983 | Roy | 623/2 |
| 4,820,299 | 4/1989 | Philippe et al. . | |
| 5,078,739 | 1/1992 | Martin . | |
| 5,197,980 | 3/1993 | Gorshkov et al. | 623/2 |
| 5,207,707 | 5/1993 | Gourley | 623/2 |
| 5,397,347 | 3/1995 | Cuilleron et al. | 623/2 |

FOREIGN PATENT DOCUMENTS 0383676   8/1990   European Pat. Off. .

*Primary Examiner*—Michael J. Milano
*Attorney, Agent, or Firm*—Burns, Doane, Swecker & Mathis, L.L.P.

[57] ABSTRACT

A cardiac valve includes a sleeve or ring having an inlet end and an outlet end and which is provided with a central opening (4), and openable and closable flaps having for their purpose to allow flow of blood through the central opening (2) in one direction, the flaps (9a–c) being designed as circle segments, where the sector angle has the value 360°/n, where n is the number of circle segments and is 3, 4, 5 or 6. The flaps (9a–c) are at their outer edges pivotably connected to the inside of the ring (3) at the inlet end thereof, in that each flap (9a–c) is connected to the ring (3) by means of a hinge which is arranged in the center of the outer edge of the flap and which is accommodated in a recess in the ring (3), whereby the flaps in a closed position cooperate to form a sealing body and in an open position allow a free passage of blood.

21 Claims, 1 Drawing Sheet

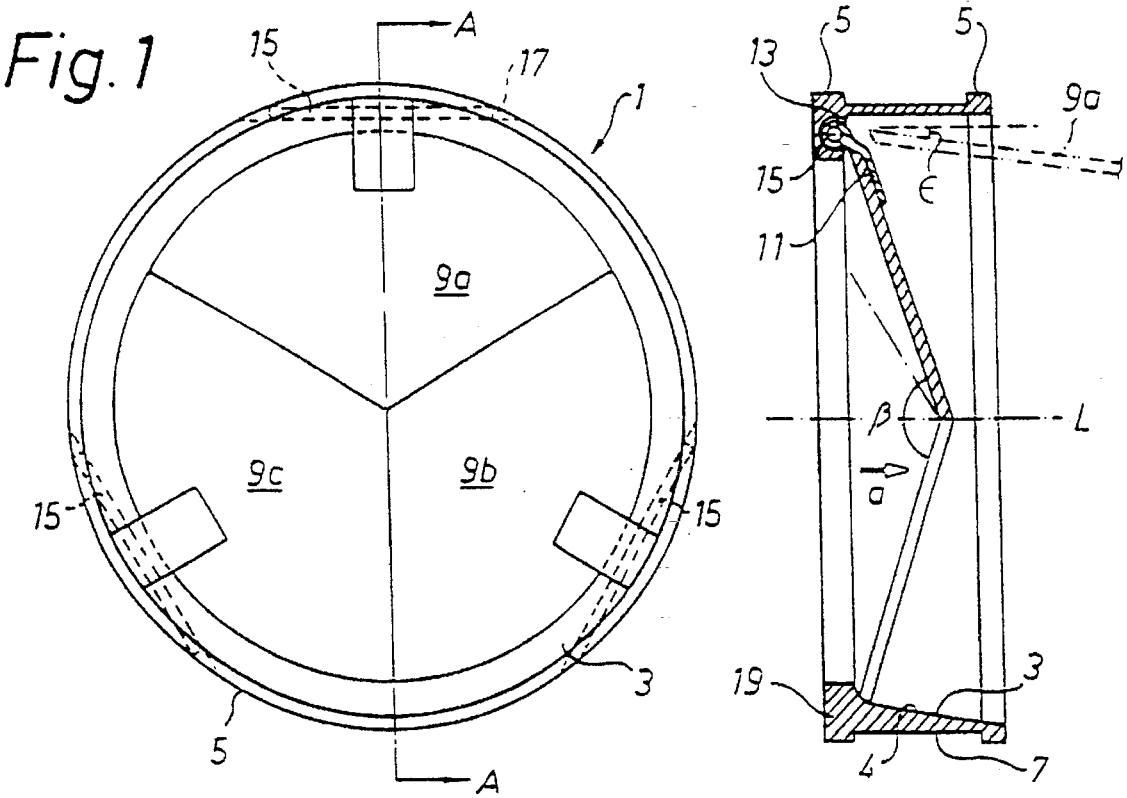
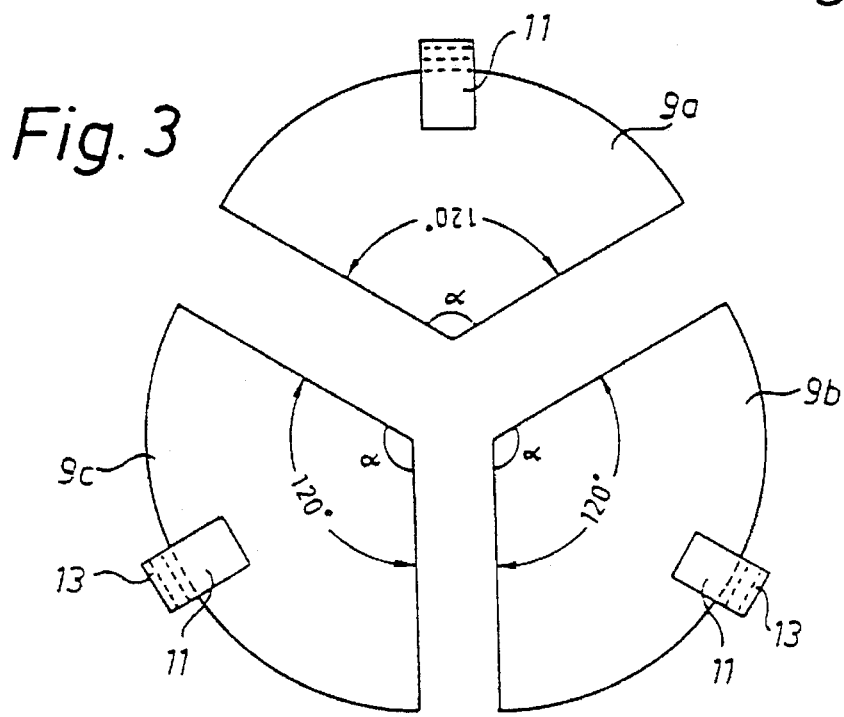

CARDIAC VALVE WITH RECESSED VALVE FLAP HINGES

This application is a continuation of application Ser. No. 08/302,697, filed as PCT/SE93/00219, Mar. 11, 1993 published as WO93/17637, Sep. 16, 1993 now abandoned.

FIELD OF THE INVENTION

The present invention relates to a back valve, more particularly a cardiac valve, so called heart valve, intended to allow flow of blood in one direction in a path of blood in connection to the heart of a living mammal, including man.

BACKGROUND OF THE INVENTION

Cardiac valves, so called heart valves, are found in a number of embodiments made both of wholly artificial materials, such as titanium, pyrolytic carbon or the like, or manufactured from natural tissue of porcine or bovine origin, said materials being treated in a chemical manner so as to obtain desirable properties. All hitherto known back valves for such intended function are associated with severe disadvantages, among which the following may be mentioned.

The designs not based on natural tissue are all made as more or less complicated constructions which result in risk of failure or unsatisfactory function in other ways. Known valves are, furthermore, designed so as to occupy, in an open position, a essential part of the flow cross-section, thus offering resistance to the flow of blood. Many of the known valves are furthermore designed in an asymmetric way with concomitant inconveniences. Furthermore, the prior art cardiac valves have a design where protruding parts disturb the flow of blood and also result in undesired epithelial growth. Finally, it can be mentioned that known valves often are associated with inertia in their opening or closing movement which substantially reduces their efficiency.

Examples of prior art designs are found in U.S. Pat. Nos. 4,820,299 and 5,078,739. These known cardiac valves are subject to the disadvantages indicated above.

SUMMARY AND OBJECTS OF THE INVENTION

The present invention has for a purpose to provide a cardiac valve, wherein the disadvantages of the prior art are eliminated or at any rate essentially reduced.

Another object of the invention is to provide a cardiac valve which in an open position offers low resistance to the flow of blood in view of the fact that the opening ratio, i.e. the ratio between the open valve passage and the cross-section in association with the valve position, is high.

Yet another object of the invention is to provide a valve showing a symmetric opening pattern, so that the flow of blood will not be disturbed in a non-desirable manner.

Still another object of the invention is to provide a cardiac valve having the capability of rapid opening and closing resulting in improved efficiency.

Another object of the invention is to provide a cardiac valve having a minimum of protruding parts whereby undesired epithelial growth is prevented or at least radically reduced.

For these and other objects which will be clear from the following description the cardiac valve according to the invention comprises ring shaped member, for example, a a sleeve or a ring, having an inlet end and an outlet end and which is provided with a central opening, and openable and closable flaps having for their purpose to allow flow of the blood through the central opening of the ring in the one direction but to prevent flow of the blood in an opposite direction. The invention is characterized in that the flaps are designed as circle segments, the sector angle designated a having the value 360°/n, where n is the number of circle segments. Said flaps are at their outer edge pivotably connected to the inside of the ring at said inlet end thereof, whereby said flaps in a closed position cooperate to form a sealing body and in an open position allow a free passage of blood.

The number of circle segments is at least three and at most six, and it is particularly preferred that the number of flags is three so that the design shall be as simple as possible.

The flaps are preferably designed as curved elements so that they together in a closed position form a cone having an obtuse peak angle designed β. For practical reasons this peak angle is at most about 180° and suitably lies within the range about 150°–175°. In this manner sealing cooperation between the flaps will be obtained in a closed position.

In accordance with the present invention each flap is connected to the inside of the ring by means of a hinge which is arranged in the center of the outer edge of the flap and which is accomodated in a recess in said ring. For the purpose of avoiding operational disturbances in the use of the cardiac valve it is suitable to design the attachment to the ring in such a manner that a certain flap alone cannot be folded to a position substantially exceeding the position, as seen in the closing direction, it has in cooperation with the other flaps.

In a manner known per se it is suitable to provide the ring at its axial ends with circumferential flanges, the function of which is to form a recess, wherein a suture ring can be placed for fixation to the surrounding tissue in connection with the implantation of the cardiac valve.

For design reasons it is preferred that the ring, at said one end where the flaps are pivotably attached, is provided with one circumferential flange which is directed inwardly substantially radially, against the inwardly facing side surface of which the outer edges of the flaps rest in sealing cooperation. In this manner also the preferred situation arises that a certain flap cannot alone be folded from an open position to a position substantially exceeding the position at which all the flaps rest in sealing cooperation.

The hinge design can be of any type as long as it meets with the requirement of allowing opening and closing of the flaps. In a preferred embodiment for the sake of simplicity, each hinge contains a pin or stud which is attached to the ring in a tangentially extending aperture therein.

In order to obtain efficient closing performance it is preferred that said flaps in a fully open position take an angle ($\epsilon$) to a line parallel with a center line (L) to said ring which is greater than zero and smaller than about 7°.

With regard to the choice of material in the cardiac valve according to the invention any conventional material can be used. It is preferred to use titanium or pyrolytic carbon, optionally in combination, and the suture ring can in a usual manner be constituted by a biologically acceptable material, such as teflon, polyester, dacron, polyurethane, or the like.

BRIEF DESCRIPTION OF THE DRAWING

The present invention will in the following be further described in relation to a preferred embodiment which is shown on the appended drawing. In the drawing:

FIG. 1 shows a plan view on the cardiac valve according to the invention;

FIG. 2 shows a side view, partly in section along A—A in FIG. 1; and

FIG. 3 shows the three flaps separated and removed from the valve ring.

DESCRIPTION OF A PREFERRED EMBODIMENT

The cardiac valve generally designated 1 and shown in FIGS. 1 and 2, comprises a ring shaped member, a of a sleeve or ring 3, having a central passage 4, through which with the valve in an open position blood can pass the valve in the direction of arrow a) (FIG. 2). Furthermore, ring 3 is provided with two circumferential, outwardly extending flanges 5, one at each end of ring 3, said flanges 5 between themselves forming a recess 7 intended to accommodate the so called suture ring (not shown in the drawing).

Ring 3 accommodates three flaps 9a–c, each shaped as a circular segment as seen in the plane of the paper, where thus the sector angle α has a value 360/3, i.e. 120°. With their curved or arcuate form flaps 9a–c form a conical body having a peak angle β (FIG. 2) which in the example shown is about 150°. This peak angle may of course be substantially larger but does suitably not exceed 180°.

Each flap 9 is at the outer edge of the circular segment provided with a hinge 11 having an enlarged outer end 13 to accommodate a hinge pin or stud 15 for providing the intended function. It is important to note that each hinge 11 is accomodated in a recess on the inside of the inlet side of ring 3. In this manner the presence of protruding parts will be avoided thereby preventing disturbing epithelial growth in the cardiac valve upon implantation. Pin or stud 15 is in the embodiment shown held in an aperture 17 extending tangentially through ring 3 enabling exterior assembly.

For practical reasons ring 3, at the end of the pivotable attachment of flaps 9a–c, provided with a radially inwardly directed circumferential flange 19, and the edge of flaps 9a–c rest in sealing cooperation against the inwardly directed side surface of said flange. This flange 19 has furthermore for its function to prevent that each separate flap in the closing direction cannot move past the position according to FIG. 2 determined by flaps 9a–c in sealing cooperation.

In FIG. 2 flap 9a is shown in open position by dotted lines. In order to obtain a maximum cross section for the flow of blood with the valve in an open position, while yet obtaining efficient closing of the valve, it is preferred that the angle ε is greater than zero and smaller than about 7°. In the embodiment shown the angle ε is about 5°. Said angle ε refers to a line parallel to the center line L of ring 3.

The embodiment of the cardiac valve according to the present invention as described above has several important advantages as compared to the prior art. Thus, the symmetry in the arrangement of the flaps means that the flow pattern with the valve in an open position becomes symmetric so that non-desirable turbulence in connection with the flow of the blood will be prevented. Furthermore, the design means that the opening ratio of the valve is very high, for example exceeding 90%, in relation to the free cross-section of the blood vessel in question. In this manner a minimum hindrance to the flow of the blood will be obtained with the valve in an open position. Furthermore, the design of the valve is simple and reliable and malfunction can therefore be eliminated. Finally, the described design means that the valve operates with very short opening and closing times, which is essential for effective function.

It can be added that the cardiac valve according to the present invention can be used both in aorta and as a mitral valve or otherwise in blood paths where a back valve function is required.

The present invention is not restricted to the embodiment described above with regard to details of construction or otherwise. It can, of course, be modified within the frame of the definition found in the appended claims.

I claim:

1. A cardiac valve, comprising:

a ring shaped member having an inlet end and an outlet end and defining a central passage;

a plurality of flaps to allow flow of blood through the central passage in one direction, the flaps being formed as segments of a circle with a curved outer edge and straight side edges, where a sector angle defined by the side edges of each segment has a value 360°/n, where n is the number of flaps and is selected as one of 3, 4, 5, or 6,; and, a plurality of hinges to connect the flaps to the ring shaped member, each flap having a hinge fastened at a center of the outer edge of the flap, each hinge being pivotably attached in a recess in an inner surface of said ring shaped member radially outward of the central passage, and each hinge including a pin or stud which is attached to the ring shaped member in a tangentially extending aperture in the recess;, wherein said flaps in a closed position cooperate to form a sealing body closing said central passage and in an open position allow a free passage of blood through said central passage.

2. The cardiac valve according to claim 1, wherein the number of flaps is 3.

3. The cardiac valve according to claim 1, wherein the flaps are arcuate so as to form in the closed position a cone having an obtuse peak angle β.

4. The cardiac valve according to claim 3, wherein said peak angle β lies within the range of about 150° to 175°.

5. The cardiac valve according to claim 1, wherein the ring shaped member includes means to prevent the flaps from pivoting to a position substantially exceeding the closed position forming the sealing body in cooperation with the other flaps.

6. The cardiac valve according to claim 1, wherein the ring shaped member is shaped at the inlet and outlet ends with circumferential flanges defining a radially outwardly facing recess to accommodate a suture ring for fixing the valve to surrounding tissue.

7. A cardiac valve according to claim 1, wherein the ring shaped member at said inlet end thereof is provided with a radially inwardly directed circumferential flange, the outer edges of the flaps sealingly engaging an inwardly facing side surface of said flange in the closed position.

8. A cardiac valve according to claim 1, wherein the valve is made of a material selected from the group comprising titanium and pyrolitic carbon.

9. A cardiac valve according to claim 1, wherein said flaps in a fully open position are at an angle to a line parallel with a center line of said ring shaped member which is greater than zero and less than about 7°.

10. The cardiac valve according to claim 2, wherein the flaps are arcuate so as to form in the closed position a cone having an obtuse peak angle β.

11. The cardiac valve according to claim 2, wherein the ring shaped member includes means to prevent the flaps from pivoting to a position substantially exceeding the closed position forming the sealing body in cooperation with the other flaps.

12. The cardiac valve according to claim 3, wherein the ring shaped member includes means to prevent the flaps from pivoting to a position substantially exceeding the closed position forming the sealing body in cooperation with the other flaps.

13. The cardiac valve according to claim 4, wherein the ring shaped member includes means to prevent the flaps from pivoting to a position substantially exceeding the closed position forming the sealing body in cooperation with the other flaps.

14. A cardiac valve according to claim 2, wherein the ring shaped member at said inlet end thereof is provided with a radially inwardly directed circumferential flange, the outer edges of the flaps sealingly engaging an inwardly facing side surface of said flange in the closed position.

15. A cardiac valve according to claim 3, wherein the ring shaped member at said inlet end thereof is provided with a radially inwardly directed circumferential flange, the outer edges of the flaps sealingly engaging an inwardly facing side surface of said flange in the closed position.

16. A cardiac valve according to claim 4, wherein the ring shaped member at said inlet end thereof is provided with a radially inwardly directed circumferential flange, the outer edges of the flaps sealingly engaging an inwardly facing side surface of said flange in the closed position.

17. A cardiac valve according to claim 5, wherein the ring shaped member at said inlet end thereof is provided with a radially inwardly directed circumferential flange, the outer edges of the flaps sealingly engaging an inwardly facing side surface of said flange in the closed position.

18. A cardiac valve according to claim 2, wherein the ring shaped member at said inlet end thereof is provided with a radially inwardly directed circumferential flange, the outer edges of the flaps sealingly engaging an inwardly facing side surface of said flange in the closed position.

19. A cardiac valve according to claim 3, wherein the ring shaped member at said inlet end thereof is provided with a radially inwardly directed circumferential flange, the outer edges of the flaps sealingly engaging an inwardly facing side surface of said flange in the closed position.

20. A cardiac valve according to claim 4, wherein the ring shaped member at said inlet end thereof is provided with a radially inwardly directed circumferential flange, the outer edges of the flaps sealingly engaging an inwardly facing side surface of said flange in the closed position.

21. A cardiac valve, comprising:
a ring shaped member having an inlet end and an outlet end and having a circumferential flange on an inner surface defining a central passage;
a plurality of flaps to allow flow of blood through the central passage in one direction, the flaps being formed as segments of a circle with a curved outer edge and straight side edges meeting at a point, wherein a sector angle formed by the side edges has a value 360°/n, where n is the number of flaps and is selected as one of 3, 4, 5, or 6;
a plurality of hinges to connect the flaps to the ring shaped member, each flap having a hinge fastened at a center of the outer edge of the flap, each hinge being pivotably attached in a recess in the flange, the recess being radially outward of the central passage, and each hinge including a pin or stud which is attached to the ring shaped member in a tangentially extending aperture in the recess;
wherein the outer edges of the flaps are disposed radially outward of the central passage and wherein said flaps in a closed position mutually abut on the side edges to form a sealing body closing said central passage and in an open position allow a free passage of blood through said central passage.

* * * * *